United States Patent [19]

Castor

[11] Patent Number: 5,440,055
[45] Date of Patent: Aug. 8, 1995

[54] METHOD AND APPARATUS FOR EXTRACTING TAXOL FROM SOURCE MATERIALS

[75] Inventor: Trevor P. Castor, Arlington, Mass.

[73] Assignee: Aphios Corporation, Woburn, Mass.

[21] Appl. No.: 30,696

[22] Filed: Mar. 12, 1993

[51] Int. Cl.6 ............................................. C07D 305/14
[52] U.S. Cl. .................................................... 549/510
[58] Field of Search ................................ 549/541, 510

[56] References Cited

FOREIGN PATENT DOCUMENTS 0521675 1/1993 European Pat. Off. .

OTHER PUBLICATIONS

Jennings, David W., et al, Supercritical Extraction of Taxol From the Bark of *Taxus Brefifolia,* May 1991, pp. 1–21, Georgia Institute of Technology, Atlanta, Ga.

Primary Examiner—José G. Dees
Assistant Examiner—Joseph M. Conrad, III
Attorney, Agent, or Firm—Wolf, Greenfield & Sacks

[57] ABSTRACT

Method and apparatus are described for isolating taxoids from taxoid containing source materials. The method and apparatus isolate taxoids from waxes and other constituents of the ornamental yew tree needle with the use of critical or near critical fluids.

21 Claims, 5 Drawing Sheets

METHOD AND APPARATUS FOR EXTRACTING TAXOL FROM SOURCE MATERIALS

FIELD OF INVENTION

The present invention relates to methods and apparatus for extracting and purifying taxol and other taxoids from source materials. The method and apparatus feature critical and near critical fluids to extract and purify taxol and other taxoids from needles and other parts of the yew tree.

BACKGROUND OF THE INVENTION

Numerous compounds showing antineoplastic activity have been identified in the organic solvent extracts of plant material, microorganisms and marine organisms. Further investigation into the utility of these compounds as chemotherapeutic and anti-HIV agents has been hampered by their low natural natural abundance and the inefficiencies of conventional extraction techniques. An example of one such compound is taxol (NSC 125973), a diterpene plant product derived from the western yew *Taxus brevifolia*. This drug, currently in clinical trials, has exhibited a striking 30 to 40% response rate against advanced cases of ovarian and a number of other cancers. This drug is, however, in short supply.

Currently, taxol is extracted with organic solvents from the milled bark of *T. brevifolia* in three major steps and chromatographically purified in four major steps. The extraction process begins with milled bark which is percolated three times with methanol at 50° to 55° C. The extract is then concentrated in methanol. Next, the concentrated methanol extract is partitioned between methylene chloride and water. The methylene chloride fraction, containing taxol, is concentrated. The methylene chloride concentrate is dissolved in 50/50 acetone:hexane, and the mixture is filtered to remove insolubles. This organic extraction process yields an amber colored syrup with a solids content which is about 1.3% of the milled bark.

The conventional purification is performed in four major steps. First, the acetone:hexane mixture from the extraction process is chromatographed on Florisil columns in a 70/30 hexane:acetone mixture to separate the taxol containing fractions. The taxol fractions are then concentrated to dryness. This step may be repeated as many as nine times. Second, taxol concentrates are crystallized from a methanol:water mixture and then recrystallized from an acetone:hexane mixture yielding 85 to 95% pure taxol. Third, the taxol is chromatographed on silica gel packed with either 2.5% isopropanol or 2.5% n-butanol in methylene chloride to yield approximately 98% pure taxol. Fourth, the taxol is dissolved in acetone, the solution filtered, and taxol recrystallized from an acetone:hexane mixture.

This organic phase extraction and chromatographic purification process yields 99% pure taxol which is about 0.014% of the milled bark. The production of taxol by this technique is encumbered by the following: (i) time consuming extraction and purification procedures; (ii) long residence times in a harsh environment; and (iii) low overall yields. Also the bark of *T. brevifolia* is usually obtained from mature trees (100 to 200 years old). The bark is difficult and costly to harvest, and is in limited supply. That tree is in danger of extinction. A significant amount of research is being conducted to find alternate manufacturing routes and raw material sources. Some of the alternate manufacturing routes include total synthesis and semi-synthesis from a closely-related taxoid, 10-deacetyl baccatin III. Alternate sources include needles of the ornamental yew, twigs, sprouts and plant cell cultures. With the exception of total synthesis which has not yet been accomplished and which may prove difficult to commercialize, these techniques all require extraction and purification of taxoids from a biomass source.

The needle of the ornamental yew may prove to be a very attractive raw material resource. The needle contains high quantities of taxoids, and is a renewable resource which can be readily cultivated in nurseries and farms.

However, the needles present additional processing challenges. The needles contain a significant amount of waxes and nonpolar constituents which are extracted into organic solvents. Some of the more nonpolar waxes can be removed by a solvent prewash with hexane. However, some compositions closely related to taxoids coextract with taxol in the major conventional solvent extraction step using methylene chloride and methanol mixtures. The total mass extracted from the needles by organic solvent may range from 35 to 42% compared to 25% for the bark. The vastly larger percentage is not an indication of greater amount of taxol but of the impurities which coextract. The virgin needles also contain a substantial amount of water (about 60%).

The taxol extraction and purification steps for needles thus become much more complicated and time consuming than the previously described process for bark.

SUMMARY OF THE INVENTION

Embodiments of the present invention are directed to methods and apparatus for extracting and purifying taxol and other taxoids from taxoid containing source materials having waxes and other constituents. The embodiments of the present invention have particular application in extracting taxoids, such as taxol, from the needles of the yew tree. The embodiments feature critical or near critical fluid.

As used herein, the term "critical fluid" refers to a fluid at or above its critical pressure and at or above critical temperature. A supercritical fluid refers to a fluid which is above its critical pressure and above its critical temperature. Thus, the term "critical fluid" encompasses the subject matter of the term "supercritical fluid." The term "near critical fluid" refers to a fluid which approaches but is not at the critical pressure and/or critical temperature; and in particular such fluids which are at or above critical pressure but below critical temperature. Near critical fluid is used to denote a fluid which has a density which is similar to that of a critical fluid. This application will use the term "CoNC fluid" for convenience in referring to critical or near critical fluids.

One embodiment of the present invention features a method of extracting taxoids from taxoid containing source materials. The method has particular application where the source materials have waxes and other constituents which may coextract with taxoids used in conventional solvent extraction techniques. The method comprises the steps of subjecting the source material to dewaxing conditions. Dewaxing conditions comprise subjecting the source material to a first fluid. The first fluid is a nonpolar CoNC fluid. The waxes dissolve in the first fluid to form a wax laden extractant and a dewaxed source material. The method further comprises the step of removing taxoids from the dewaxed source material by subjecting the dewaxed source material to a second fluid to form a taxoid extractant and residual material. The second fluid is a mixture of a CoNC fluid and a polar cosolvent. The wax laden extractant and the taxoid extractant are subjected to chromatography means to form a taxoid and one or more eluant.

As used herein, the term "nonpolar" suggests a material with a dipole movement of 0.0 to 0.1 Debyes. The term "polar" suggests a material with a dipole movement of approximately 0.1 to 0.1 to 1.7 Debyes.

Preferably, eluants are depressurized to separate taxoids that have coeluted. Taxoids which coelute precipitate from the CoNC fluid upon depressurization. Taxoids, isolated upon depressurization of the CoNC fluid, are purified by chromatographic techniques to form purified taxoids.

Preferably, the depressurized first and second fluids are passed through an extractant cooler to form a CoNC fluid substantially free of taxoids which is then recycled, and waste, which is removed.

The term "substantially free of taxoids" is used in the sense of having less taxoids compared to the starting material of the process step.

Chromatography means comprise one or more chromatographic columns. Taxoids absorbed on a first column, during the passage of second fluid, are eluted with a relatively polar mixture of an organic solvent (hexane:n-propanol:methanol ternary gradient) or a third fluid. The third fluid is comprised of a CoNC fluid and a cosolvent of different type or concentration that the second fluid. Fractions which are identified as containing large amounts of taxoids are subjected to further chromatography with additional columns. Fractions which are identified as containing nontaxoids or small amounts of taxoids are treated as waste or reprocessed and recycled as an elutant through additional chromatographic processes. Fractions with small amounts of taxoids, which are not waste, are subjected to a fourth fluid. The fourth fluid is comprised of a CoNC fluid and a polar cosolvent. The pressure and/or the temperature of fourth fluid is either higher or lower than the third fluid to remove nontaxoid solutes. Thereafter, the temperature and pressure of the fourth fluid is adjusted and the fluid recycled through the first chromatography column.

Taxoid containing fractions are subjected to further columns and are then eluted by a relatively nonpolar mobile phase comprising an organic solvent mixture or fifth fluid. The fifth fluid is comprised of a CoNC fluid and a nonpolar cosolvent. Suitable organic solvent mixtures comprise methanol and acetonitrile mixtures. Fractions containing purified taxol and closely related taxoids are collected. The mobile phase containing no taxoids or small amounts of taxoids are sent to waste or reprocessed and recycled. CoNC fluid/solvent mixtures with no identifiable taxoids are reprocessed by changing the pressure and the temperature of the mixture to allow impurities to leave the solution to produce a CoNC fluid and CoNC fluid/mixture cosolvent suitable for recycling.

Preferably, the CoNC fluid is selected from the compounds carbon dioxide; nitrous oxide; alkanes, such as propane; alkenes, such as ethylene; and fluorocarbons, such as chloradifluoromethane. These compounds are gases at normal room temperatures and pressures. However, at low temperatures, and pressures above atmospheric pressure, these compounds have the ability to form CoNC fluids.

Preferably, polar cosolvents are selected from the group of polar solvents consisting of methanol, ethanol, butanol, propanol, methylene chloride, and acetone.

Embodiments of the present method are ideally suited to extract taxoids consisting of taxol, cephalomannine, baccatin III, 10-deacetyl baccatin III, deacetyltaxol and deacetyl-7-epitaxol and derivatives and precursors thereof. Embodiments of the present invention allow for the isolation and extraction of taxol and taxol like compositions from a renewable source material such as needles.

Optionally, the needles are first dried to remove water and processed to expand the effective surface area of the material. Typical processing to expand the surface area comprises grinding or milling.

One embodiment of the present invention features an apparatus for extracting taxoids from taxoid containing source materials having waxes and other constituents. The apparatus comprises a chamber adapted to receive source materials, a first fluid, and a second fluid. The apparatus further comprises a source of a first fluid in communication with the chamber. The first fluid comprises a CoNC fluid. The source of first fluid is capable of directing first fluid into the chamber to subject the source material to dewaxing conditions. The first fluid dissolves the waxes of the source material to produce a wax containing extractant and a dewaxed source material. The apparatus further comprises a source of a second fluid. The second fluid is a mixture of a fluid and a polar cosolvent. The source of the second CoNC fluid is in communication with the chamber. The source of the second fluid is capable of directing the second fluid into the chamber to form a taxoid extractant and waste material. The chamber is in communication with chromatography means for receiving the wax laden extractant and the taxoid extractant from the chamber to form a eluant and concentrated taxoids.

Preferred chromatograph means comprise one or more columns. Preferably, the columns are in communication with depressurization means to reduce the pressure of the eluant. Upon depressurization, taxoids, which coeluted with the eluant, are released and can be further processed.

Preferably, taxoids produced upon passage through the depressurization means are purified to form purified taxoids.

Preferably, depressurization means is in communication with an extractant cooler for receiving the eluant from the depressurization means. Upon cooling, impurities are removed from the eluant and the eluant can be recycled.

Preferably, the first and second fluids are recycled after removal of taxoids and waste materials by conduits and pump means in communication with the chromatography means.

One embodiment of the present apparatus features a conduit in communication with one or more columns of the taxoid purification means and in communication with the source of the first fluid or the second fluid. The conduit is adapted to receive the second fluid flowing through the columns until taxoids elute. The apparatus further comprises means for directing the second fluid from such conduit, to a second column as the taxoids elute, to remove such taxoids and produce a taxoid free CoNC fluid.

Preferably, the taxoid free CoNC fluid is depressurized allowing impurities to leave the solution to produce a second fluid suitable for recycling.

Preferably, the apparatus is adapted for receiving carbon dioxide; alkanes, such as propane; alkene, such as ethylene; fluorocarbons, such as chlorodifluoromethane; and or nitrous oxide as a CoNC fluid. Preferably, the apparatus is adapted to receive a polar solvent selected from the group consisting of methanol, ethanol, propanol, butanol, methylene chloride and acetone.

The present apparatus is ideally suited for isolation of taxoids such as taxol, baccatin III, 10-deacetyl baccatin III, cephalomannine, deacetyl-taxol and deacetyl-7-epitaxol.

Embodiments of the present invention are able to extract 0.048 wt. % taxol (99+% of available taxol) from the needles of the ornamental yew with supercritical carbon dioxide containing 20.9% methanol (at 40° C. and 1,274 psia) in only 21 minutes. The taxol recovery is surprising and unexpected. The short residence time is significant since it will dramatically impact the capital and operating costs of a commercial plant.

Embodiments of the present invention feature a quick high speed extraction through improved permeation and solvation. Compared to conventional methods, the process has improved production capacity and improved scalability. The process features greater overall efficiency and in fewer processing steps. Extractants made in accordance with the present invention feature improved product quality with minimal use of organic solvents.

The apparatus and method of the present invention can increase the availability of taxoids for research purposes and clinical trials. A preferred source material comprises needles. The present method and apparatus extracts taxoids in the presence of an impurity which impurity is typically found in needles only. However, the present method and apparatus has applications for extracting taxol from other source materials in addition to the needles of the yew plant.

Other features and advantages of the present invention will be apparent from the examination of the drawings and the detailed descriptions which follow.

DETAILED DESCRIPTION OF THE INVENTION

Embodiments of the present invention will be described as methods and apparatus for the extraction of taxol from needles of the yew tree. As used herein, yew is intended to encompass the species Taxus media and *Taxus brevifolia,* and other plants of the genus Taxus.

The present invention features the use of CoNC fluids as solvents. CoNC fluids are comprised of certain material which exist as gases at ambient conditions, such as the gases carbon dioxide and nitrous oxide. When such gases are compressed and brought to conditions near or above their critical pressures and temperatures, such gases exhibit enhanced solvating power.

A CoNC fluid exhibits a liquid-like density and at the same time gas-like properties of diffusivity and viscosity. The CoNC fluid displays a wide spectrum of solvation power because its density is strongly dependent on both temperature and pressure. Temperature and pressure can be altered to change solubility by an order of magnitude or more. CoNC fluids further exhibit ultra-low surface tension which allows facile penetration into microporous materials.

Figures 1, 1A:
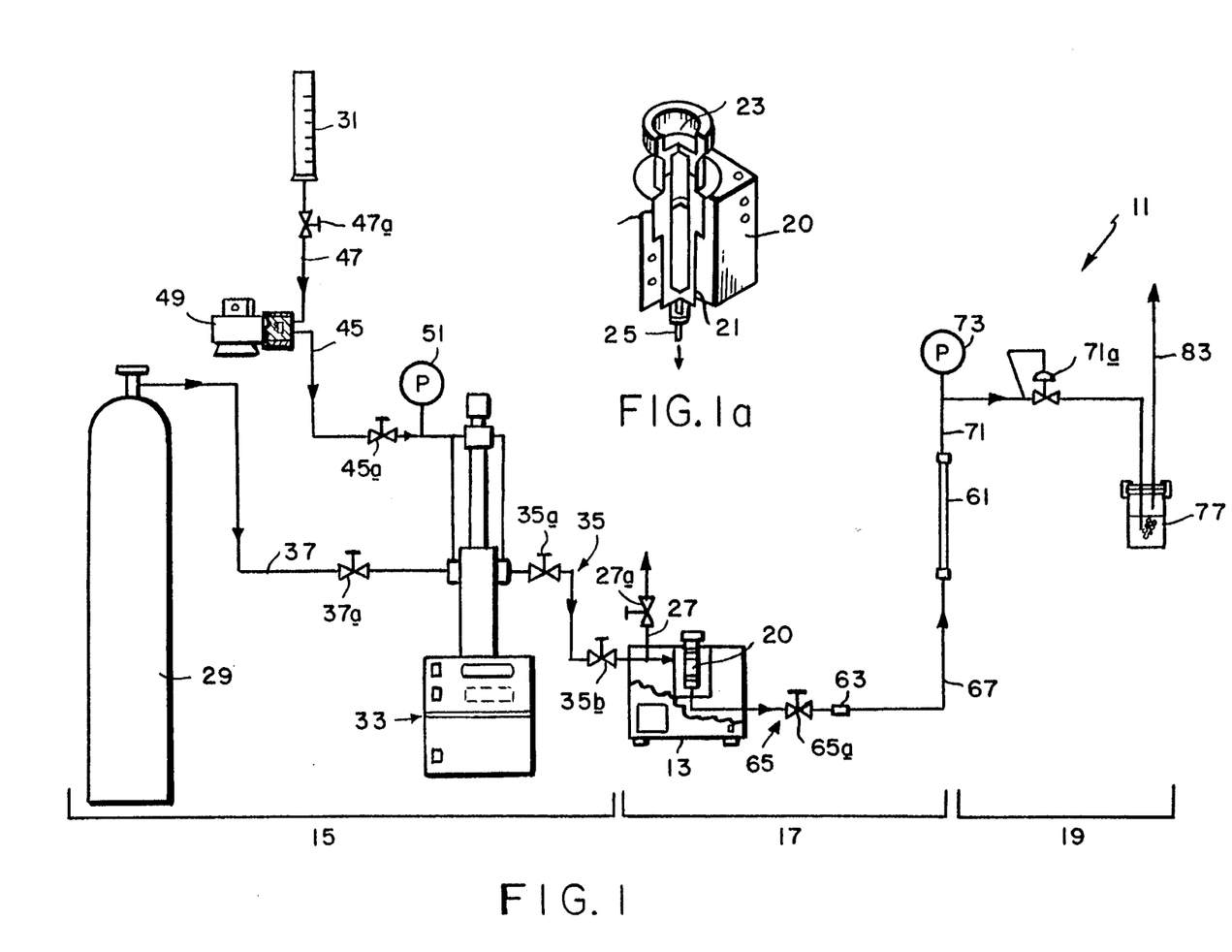
FIG. 1 depicts a schematic view of a critical fluid extraction and chromatography apparatus embodying features of the present invention.
FIG. 1a depicts the extractor assembly.

An apparatus embodying features of the present invention for performing CoNC fluid extraction of taxoids from source materials including needles, generally designated by the numeral 11, is depicted in FIG. 1. The apparatus 11 is comprised of four major elements: an extractor 13; CoNC fluid delivery assembly, generally designated by the numeral 15; chromatographic purification assembly, generally designated by the numeral 17; and pressure letdown means, generally designated by the numeral 19.

The extractor 13 is depicted in greater detail in FIG. 1A. The extractor 13 has a housing 20 which defines a chamber 21 for receiving source material. Preferably, the source material has been rendered into fine particles by milling or grinding. The chamber 21 has an inlet 23 for receiving fluid and an outlet 25 for removing fluid. An extractor shunt 27, in communication with inlet 23, allows CoNC fluid to be vented. The flow of CoNC fluid through shunt 27 is controlled by valve 27a.

The extractor 13 is equipped with thermostatic controls (not shown) for maintaining a constant temperature and an opening (not shown) for loading source material. One such extractor is known as an Isco Model SFX 2-10 extraction unit.

The inlet 23 of chamber 21 is in communication with the CoNC fluid delivery assembly 15. The CoNC fluid delivery assembly 15 is comprised of the following major elements: CoNC fluid vessel 29, cosolvent vessel 31 and syringe pump 33. Syringe pump 33 is in communication with the inlet 23 of chamber 21 via conduit 35. Two valves 35a and 35b control flow in conduit 35. Syringe pump 33 is adapted to receive cosolvent from cosolvent vessel 31 and a CoNC fluid from CoNC fluid vessel 29. Syringe pump 33 is in communication with critical fluid vessel 29 via conduit 37. A valve 37a controls the flow of CoNC fluid in conduit 37.

Syringe pump 33 is in communication with cosolvent vessel 31 via two conduits 45 and 47. Conduit 45 is in direct communication with syringe pump 33 and cosolvent pump 49. The flow of cosolvent to the syringe pump 33 is controlled by a valve 45a. Pressure in conduit 45 is monitored by a pressure gauge 51.

Conduit 47 is in direct communication with cosolvent pump 49 and cosolvent vessel 31. Cosolvent is received by cosolvent pump 49 from conduit 47 and forced through conduit 45. The flow of cosolvent to cosolvent pump 49 via conduit 47 is controlled by valve 47a.

Extractor outlet 25 is in communication with chromatographic purification assembly 17. Chromatographic purification assembly 17 is comprised of two major elements, an HPLC column 61 and filter element 63. Filter element 63 is a 5 micron filter, in communication with outlet 25 via an outlet conduit 65. CoNC fluid flowing from the extractor through conduit 65 is filtered by filter element 67. CoNC fluid enters the HPLC column 61 via conduit 67. HPLC column 61 is a normal phase HPLC column.

The CoNC fluid flows from the HPLC column 61 to pressure letdown assembly 19. CoNC fluid leaves HPLC column 61 via conduit 71. Pressure within the outlet conduit 71 is monitored by a pressure gauge 73 and controlled by pressure letdown valve 71a.

The depressurized CoNC fluid enters a collection vessel 77. Collection vessel 77 contains a solid or liquid entrapment phase, such as a 50:50 mixture of methylene chloride and methanol. Collection vessel 77 retains taxoids held in the CoNC fluid, as well as any cosolvent which does not vaporize. CoNC fluid is vented through a vent 83.

In operation, a dried, and milled or ground source material, such as milled or ground needles of the yew tree, are placed within the chamber 21 of the extractor 13. The source material first receives a flow of a first fluid, such as CoNC carbon dioxide. The first CoNC fluid is relatively nonpolar. The waxes and other constituents of the source material are dissolved in the CoNC fluid and are removed through outlet 25 of chamber 21 and through conduit 65. The wax and other nontaxoid constituents of the source material held in the CoNC fluid are collected in collection vessel 77 and discarded. The CoNC fluid is vented through vent 83.

Next, a second fluid is formed by combining a polar cosolvent such as methanol, ethanol, or acetone, with a CoNC fluid. Syringe pump 33 receives the second fluid which is injected into the extractor chamber 21 via conduit 35. The second fluid removes taxol and other taxoids from the source material. The taxoid laden second fluid is removed from chamber 21 through outlet 25 to the HPLC column 61 of chromatographic assembly 17. The HPLC column 61 removes taxol and other taxoids such as 10-deacetyl baccatin-III from the second CoNC fluid.

Taxoids and other impurities which coelute in the second fluid are collected in collection vessel 77. The second CoNC fluid and cosolvent is depressurized at pressure letdown valve 71a, allowing the taxoids and other impurities to leave solution. CoNC fluid is vented from the collection vessel 77 via vent 83.

Figure 2:
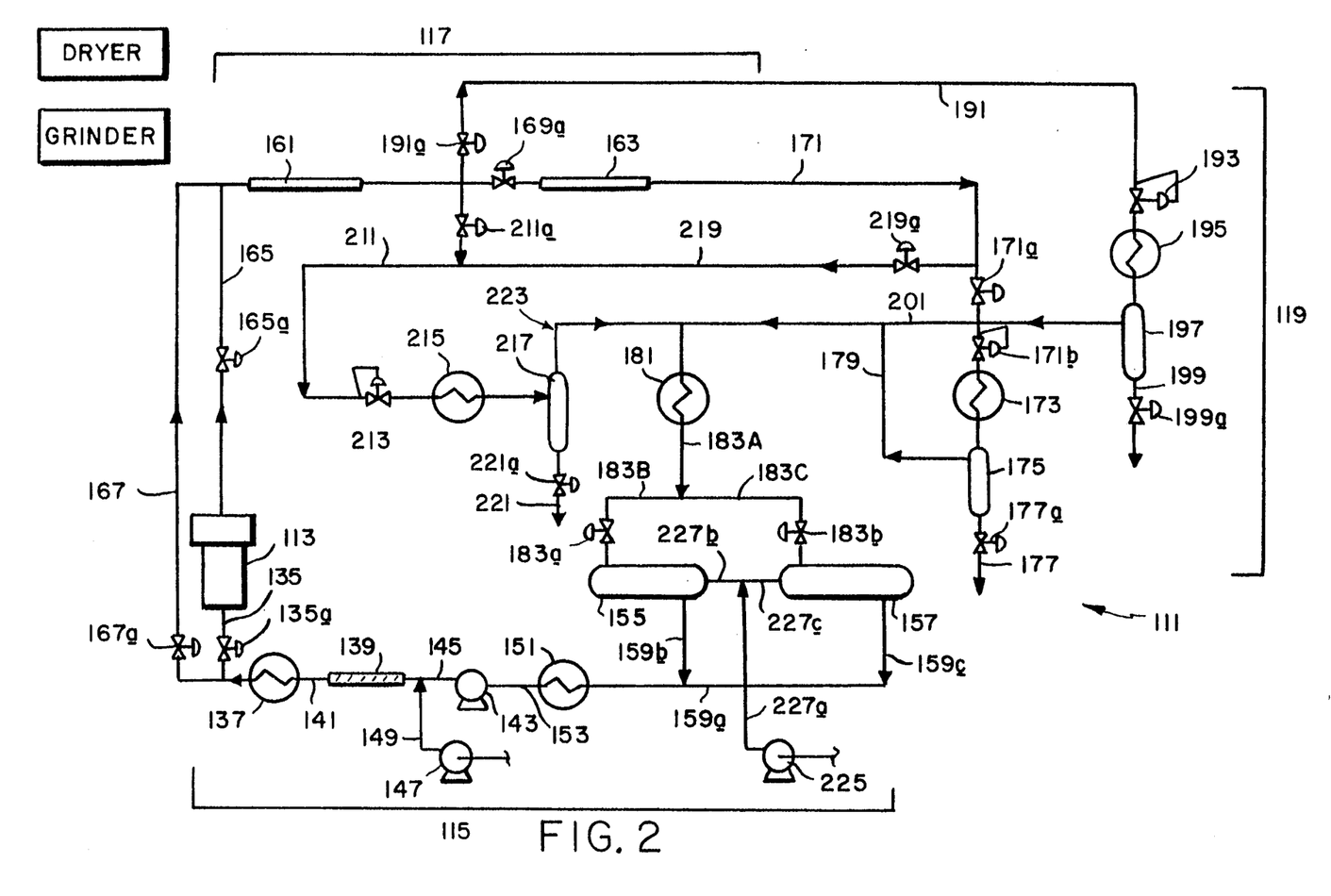
FIG. 2 depicts a critical fluid extraction and chromatography apparatus embodying the features of the present invention, including recycling of reagents, supercritical fluid and cosolvents.

An apparatus embodying features of the present invention, featuring CoNC fluid and cosolvent recycling, is depicted in FIG. 2. The taxoid extraction apparatus, generally designated by the numeral 111, is comprised of the following major elements: an extraction assembly 113; a CoNC fluid assembly, generally designated by the numeral 115; chromatographic assembly, generally designated by the numeral 117; and pressure letdown assembly, generally designated by the numeral 119.

Extraction chamber 113 has features similar to features of extraction chamber 13 described with respect to FIG. 1. That is, extraction chamber 113 has an inner chamber (not shown) having an inlet and an outlet (not shown). The chamber of the extraction assembly is capable of holding source materials containing taxoids. Preferably, the source materials are dried and optionally reduced to particulate form by drying and grinding assemblies (not shown).

The extraction assembly 113 receives CoNC fluid via conduit 135 in communication with the inlet of the chamber (not shown). Flow through conduit 135 is controlled by valve 135a. Conduit 135 is in communication with preheater 137. Preheater 137 adjusts the temperature of the CoNC fluid and cosolvent mixture. Preheater 137 is in communication with static mixer 139 via conduit 141. Static mixer 139 mixes CoNC fluid and cosolvent to a homogenous mixture forming a second CoNC fluid.

Static mixer 139 is in communication with circulation pump 143 via conduit 145, and cosolvent make-up pump 147 via conduit 149. Cosolvent make up pump 147 is in communication with a vessel (not shown) containing cosolvent. Cosolvent pump 147 is capable of injecting cosolvent into conduit 141 to adjust the concentration of cosolvent in the CoNC fluid fed to extraction assembly 113.

Circulation pump 143 is in communication with a subcooler 151 via conduit 153. Subcooler 151 is adapted to cool CoNC fluid and CoNC fluid/cosolvent mixtures to adjust the temperature. Subcooler 151 is in communication with a reservoir of CoNC fluid 155 and a reservoir, containing a second CoNC fluid comprising a CoNC fluid/cosolvent mixture, via conduits 159a, 159b and 159c.

The outlet (not shown) of the chamber of the extractor 113 is in communication with chromatographic assembly 117. Chromatographic assembly 117 is comprised of the following major elements: a first adsorption column 161 and a second adsorption column 163. First adsorption column 161 is in communication with outlet (not shown) of the chamber of the extraction assembly 113 via conduit 165. Valve 165a controls the flow of the second CoNC fluid in conduit 165.

First adsorption column 161 is adapted to retain taxol, baccatin III, 10-deacetyl baccatin III, cephalomannine and other taxoids of interest extracted from source materials. First adsorption column 161 is in communication with a source of CoNC fluid and CoNC fluid/cosolvent mixture via shunt 167. Shunt 167 is in communication with the CoNC fluid reservoir 155 and CoNC fluid/cosolvent reservoir 157. Valve 167a controls fluid flow through conduit 167. Shunt 167 allows CoNC fluid and CoNC fluid/cosolvent mixtures to elute taxoids adsorbed by first adsorption column 161.

First adsorption column 161 is in communication with a second adsorption column 163 via conduit 169. Valve 169a controls movement of CoNC fluid or CoNC fluid/cosolvent mixtures in conduit 169. Second HPLC column 163 is in communication with pressure letdown assembly 119. Conduit 171, of pressure letdown assembly 119, receives fluid from second adsorption column 163. Flow of fluid through conduit 171 is controlled by valve 171a. Conduit 171 carries eluted taxol and CoNC fluid/cosolvent to pressure letdown valve 171b, taxol heater 173, and a taxol separator 175. The taxol heater 173 attenuates the first fluid and the second fluid allowing taxol to separate out of solution in taxol separator 175.

Taxol is removed from taxol separator 175 through conduit 177. Valve 177a controls the flow of fluid through conduit 177. Supercritical fluid and supercritical fluid/cosolvent mixtures are removed from taxol separator 175 via a exit line 179.

Line 179 is in communication with an extractant cooler 181. Extractant cooler 181 redensifies CoNC fluid and CoNC fluid/cosolvent mixtures.

Extractant cooler 181 is in communication with first fluid reservoir 155 and second fluid/cosolvent reservoir 157 via conduits 183a, 183b and 183c. First fluid reservoir 155 contains a CoNC fluid. Second fluid reservoir 157 contains a second fluid comprising a CoNC fluid and a cosolvent. Valves 183a and 183b control fluid movement in conduits 183A, 183B, and 183C.

The taxoid 10-deacetyl baccatin III elutes from column 161 with certain CoNC fluid/cosolvent mixtures. Conduit 169 is in communication with pressure letdown assembly 119 via baccatin shunt 191. Valve 191a controls the flow of fluid through baccatin shunt 191. 10-Deacetyl baccatin III eluted from first adsorption column 161 is directed to baccatin shunt 191.

Baccatin shunt 191 is in communication with pressure letdown valve 193, baccatin heater 195 and baccatin separator 197. Pressure letdown valve 193 reduces the pressure of CoNC fluid/cosolvent mixtures. Baccatin heater 197 attenuates the CoNC fluid and CoNC fluid/cosolvent mixtures. The combination of lower pressure and moderate temperature causes 10-deacetyl baccatin III to come out of solution in baccatin separator 197.

10-Deacetyl baccatin III is removed from baccatin separator 197 via conduit 199. Valve 199a controls the movement of 10-deacetyl baccatin III from baccatin separator 197.

Baccatin separator 197 is in communication with extractant cooler 181, first fluid reservoir 155 and second fluid reservoir 157 via conduit 201. Conduit 201 is in communication with conduit 179 to recycle CoNC fluid and CoNC fluid/cosolvent mixtures.

First adsorption column 161 is in communication with pressure letdown assembly 119 via a second shunt 211. Valve 211a controls movement of CoNC fluid and CoNC fluid/cosolvent mixtures through conduit 211. Conduit 211 is in communication with a pressure letdown valve 213, extractant heater 215, waste separator 217 and shunt 219. Shunt 219 is in communication with conduit 171. Shunt 219 receives supercritical fluid and supercritical fluid/cosolvent mixtures from second adsorption column 163, for recycling. Valve 219a controls movement through conduit 219.

Conduit 211 receives substantially taxoid-free fluid and CoNC fluid/cosolvent mixtures from first HPLC column 161 and shunt 219. Pressure letdown valve 213 reduces the pressure of CoNC fluid and CoNC fluid/cosolvent mixtures flowing through conduit 211. Extractant heater 215 heats CoNC fluid and CoNC fluid/cosolvent mixture flowing through conduit 211. The reduction of pressure and addition of heat allows waste materials to come out of solution in waste separator 217.

Wastes are removed from waste separator 217 via conduit 221. Valve 221a controls movement of waste fluids through conduit 221.

Waste separator 217 is in communication with extractant cooler 181, first fluid reservoir 155 and second fluid reservoir 157, via conduit 221. Conduit 221 is in communication with conduit 179 to convey CoNC fluid and CoNC fluid/cosolvent mixtures to extractant cooler 181. Extractant cooler 181 densifies the fluids for recycling.

CoNC fluid losses are compensated by CoNC fluid makeup pump 225. CoNC fluid makeup pump 225 is in communication with first CoNC fluid reservoir 155 and second CoNC reservoir 157 via conduits 227 a, b and c. CoNC fluid makeup pump 225 is in communication with a source of CoNC fluid (not shown).

In operation using supercritical fluid carbon dioxide, dried raw material is ground and transferred to the extraction chamber of extractor 113. A preferred dried material is yew needles. The material is subjected to a dewaxing step using a first fluid. The first fluid comprises critical fluid carbon dioxide at a density of about 0.8 g/ml. Saturated liquid carbon dioxide at approximately 1,000 psi is drawn off from the first fluid reservoir 155 and slightly subcooled to avoid cavitation during pumping. The circulation pump 143 pressurizes the first fluid to the extraction pressure of 3,000 psi, and pumps it through a static mixer 139 and a preheater 137 which brings the carbon dioxide to the extraction temperature of 40° C. The nonpolar carbon dioxide extracts the nonpolar waxes and some taxoids from the raw material.

The wax laden extractant is passed through a first adsorption column 161 which retains the taxoids. The carbon dioxide passes through valve 211a through back pressure regulator 213. The carbon dioxide undergoes a pressure drop to about 1,100 psi and a concomitant drop in temperature.

The first fluid is reheated to about 40° C. in the extractant heater 215. Under these conditions, the density of the supercritical carbon dioxide is only about 0.2 g/ml so that the entrained waxes have little solubility and drop out in the waste recovery separator 217. The purified carbon dioxide is then passed to the extractant cooler 181 to be liquefied, and returned to the first CoNC reservoir 155.

The dewaxed raw material is next subjected to a taxol extraction/adsorption step using a second fluid. The second fluid comprises a mixture of supercritical carbon dioxide and a polar cosolvent, for example acetone. Second fluid is drawn from reservoir 157 by the circulation pump 143. Additional cosolvent is added to the stream to make up for losses incurred during the previous cycle. The mixed stream passes through the static mixer 139 to insure a uniform composition, and then through the preheater 137 and into the extraction vessel 113. Extraction conditions are approximately the same as used for the dewaxing step.

The extractant containing taxol, taxoids and impurities is pumped to a first adsorption column 161 where taxol and similar compounds are selectively adsorbed.

Next, the extraction chamber 113 is placed offline, to be serviced, unloaded or recharged. Taxol is eluted from the first adsorption column 161 using a third fluid. The third fluid comprises carbon dioxide and a cosolvent. The concentration of the polar cosolvent is increased in the third fluid compared to the second fluid mixture. The stream leaving the first adsorption column is directed through valve 211a until the taxol/cephalomannine band is eluting, at which point the flow is diverted through valve 169a to second adsorption column 163. Second adsorption column 163, adsorbs taxol, cephalomannine, taxoids and other impurities. As the supercritical fluid/cosolvent mixture also has the effect of desorbing the baccatin from the silica column, the eluant is directed through valve 191 to a separate depressurization loop where the baccatin is recovered in baccatin separator 197. The recovered baccatin will contain other materials which have passed through the silica column during this extraction step, and may require further purification before use.

Following baccatin recovery, the critical fluid/cosolvent mixture is passed through the extractant cooler 181 and then to the CoNC fluid/cosolvent reservoir 157 to be recycled.

Taxoid-free streams leaving adsorption columns 161 and 163 are directed through valve 219a, and subsequently undergo a pressure reduction to drop out impurities. The solvent streams then proceed to the extractant cooler 181 and the CoNC fluid/cosolvent reservoir 157 to be recycled.

Next, taxol is eluted from the second adsorption column 163 using a fourth fluid. The fourth fluid is comprised of a CoNC fluid and a polar cosolvent. The cosolvent is present at a lower concentration than the second fluid. Thus, the fourth fluid is less polar than the second fluid. Taxoids are recovered by means of pressure drop in the taxol separator 175. The CoNC fluid/cosolvent mixture is reintroduced to extractant cooler 181 for recycle. A certain amount of cosolvent will be present in the recovered taxol. This may be removed by evaporation, condensed, and recycled.

Individuals skilled in the art will recognize that the first, second, third and fourth fluids may have identical or similar CoNC fluid components, or may have different CoNC fluid components and operate on distinct circuits. Similarly, the second, third and fourth fluids may have identical or similar cosolvent components or may have different cosolvent components and operate on distinct circuits. The process and apparatus are amenable to additional chromatographic processes involving further fluids.

EXAMPLES

A. General

HPLC grade organic solvents used were acetonitrile, chloroform, hexane, methanol and methylene chloride from Baker, and acetone from EM Science. Purified toluene (Mallinckrodt), p-anisaldehyde (Sigma), butyl paraben (Sigma) and anhydrous ethanol (Baker) were also used. Critical fluid solvents used were CP grade (98% +) carbon dioxide ($CO_2$), nitrous oxide ($N_2O$), propane ($C_3H_8$) and Freon-22 or chlorodifluoromethane ($CHClF_2$) from Associated Gas Products, Everett, Mass.

Taxol standards utilized were baccatin III (lot # 330753), cephalomannine (lot # 318735) and taxol (lot #s 125973 and 125973-L/24) from the National Cancer Institute, and 10-deacetyltaxol (lot # GS-6S-170-4), 10-deacetyl-7-epitaxol (lot # GS-6S-170-3) and 7-epitaxol (lot # GS-6S-172-1) from consultant Dr. David G. I. Kingston, Virginia Polytechnic Institute and State University, Blacksburg, Va. Taxol from lot # 125973-L/24 contained an impurity and was not used as standard. Stock solutions of pure standards were made up in methanol. A mixed standard was used to evaluate coelution and peak interference with different mobile phases in the isocratic and gradient modes. A relatively pure taxol-cephalomannine side cut (lot # 624955-1/13/0) obtained from NCI was used.

Raw materials used were freshly cut 12" stems of *Taxus media* "Hicksii" from Renkema Farms, Zelenka Nursery, Grand Haven, Mich. The needles were manually removed from the stems and dried overnight in an oven at 60° C.; the solids content of the needles was typically about 40%. The dried needles were then ground into a fine powder (70 mesh) using a Janke & Kunkel 20,000 rpm grinder. HPLC analyses of taxenes were performed on a computer controlled ternary gradient system (Model 2350 pump/Model 2360 controller with a variable wavelength (Model V4) detector, Isco, Lincoln, Nebr.) and a Rheodyne Model 7125 injector. A 15 cm, 5 micron Phenyl column was utilized with a Phenyl guard column (Rainin, Woburn, Mass.). A ternary system was used as a gradient system, in which A=60% methanol, B=40% methanol/40% acetonitrile, and C=100% methanol. The flowrate was 1.0 ml/min and the wavelength was 228 nm. This gradient provided an excellent separation between all standards, and removed baccatin III far enough from the solvent front to allow quantification in some samples. An isocratic mobile phase consisting of 55% methanol:12% acetonitrile at 1.0 ml/min and detection at 228 nm was also utilized. Our HPLC analytical techniques were validated against analyses of the taxol/cephalomannine side cut by NCI and Polysciences, Inc. (Bio-Eng: 23.8% taxol and 44.3% cephalomannine versus NCI: 23.8% taxol and 43.6% cephalomannine).

Other analytical and preparative instruments used were: a single beam UV/VIS spectrophotometer (Hitachi, Model 100-10), a Soxhlet extractor with Friedrichs condenser and Whatman cellulose thimbles (VWR), a micro-rotary evaporator (Buchler Instruments, Model 4214-000), and a thin layer chromatography system with diphenyl and silica plates. The thin layer chromatography system proved to be much less sensitive than HPLC for taxoids and was thus not used to any great extent.

Usual methods for the analysis of taxol incorporate an extraction with organic solvents, partitioning into methylene chloride, and determination on a phenyl column using an acetonitrile-methanol-water mobile phase. Although these systems work well for extractions from bark samples, needle samples contain compounds which coelute with taxol in this reversed phase system. An analytical method using methanol extraction, methylene chloride partitioning, and mini-column cleanup was developed to quantify the influence of coeluting compounds on taxol purity from absorbance data at 228 nm and 280 nm.

There are several published methods for the determination of taxol in yew needles and the bark of *Taxus brevifolia*. The present examples feature an analytical method involving a simplified extraction technique, cleanup using a silica mini-column, and final quantitation using absorbance data at 228 nm and 280 nm. This method succeeds in correcting for a coeluting impurity which is not determined by previously published methods.

The HPLC system consisted of ISCO ternary gradient instrumentation (Lincoln, Nebr.) incorporating an ISCO V4 detector for routine analytical work, an ISCO S 500 detector for simultaneous quantitation at 228 and 280 nm, and a SpectraPhysics Spectra Focus Model SF101-0122 detector for generating 3-dimensional spectral scans. The silica mini-columns (01-00 SPICE Cartridges) were obtained from Rainin Instrument Company, Woburn, Mass. The silica used in column chromatography was supplied by EMScience, Cat. No. 10180-3 Silica Gel 40, 70–230 mesh.

Samples of Taxus branches were dried at 60° C. for 16–20 hours. The needles were removed from the stems, ground in a Waring blender and sieved to pass through a 70 mesh screen. Material that did not pass was reblended until a total of 90% of the sample had passed through the screen.

A ground sample (200 mg) was weighed into a 40 mL vial. Methanol (30 mL) was added and the sample was stirred overnight using a magnetic stirrer. The extract was filtered through #40 Whatman paper into a 250 mL separatory funnel containing 15 mL of water and 10 mL of methylene chloride. The extraction vessel was rinsed with 30 mL of methylene chloride and this rinsing was filtered into the separatory funnel.

The methanol-water phase was extracted with three volumes of methylene chloride (ca 50 mL each) and these extracts were transferred to a 250 mL rotary evaporation flask. Additional water or methanol was added as needed to produce or to clarify the phase separation. The extraction was continued until a total volume of 200 mL had been collected. The extract was evaporated to apparent dryness. Traces of residual water were removed by adding 20 mL of acetone followed by 25 mL of hexane and again bringing the extract to dryness. The sample was then redissolved in 8 mL of methylene chloride.

The methylene chloride solution of the extract was slowly passed through a silica mini-column and the column was washed with an additional 4 mL of methylene chloride. This washing removed waxy, nonpolar substances; the taxol was contained within a green band near the top of the column. The eluant was changed to 4% acetone in methylene chloride and the elution was stopped just as the green band began to exit from the column. The eluant was then changed to 20% acetone in methylene chloride and the taxol containing band was eluted from the column using two 10 mL portions of this solvent. The extract was taken to dryness using rotary evaporation and the residue was taken up in 2.00 mL of methanol.

The HPLC column was a Rainin 80-D15-C5 Microsorb 5 micron, 4.6 mm×15.0 cm phenyl bonded phase column with a 1.5 cm phenyl guard column. The mobile phase was 12% acetonitrile and 55% methanol—the remainder being water. The flow rate was 1.0 mL/min. A taxol standard at a concentration of 0.050 mg/mL was prepared in methanol. The injection volumes were 10 microliters for both standards and samples. Peak heights were measured in dual channel mode at both 228 nm and 280 nm and taxol was quantified using the following equation:

$$\% \text{ Taxol} = 100 \times \frac{C(\text{Standard}) \times H(\text{Sample})}{C(\text{Sample}) \times H(\text{Standard})} \times PF \quad (1)$$

where
  C=concentration in mg/mL
  H=peak height from the 228 nm channel
and
  PF=Purity Factor of the taxol peak calculated from A(280)/A(228) absorbance ratio in Equation 2 (See below)

Extracts of both Taxus needles and bark were prepared using classical organic phase extraction as well as supercritical fluid extraction. Analysis conducted in our laboratory using reversed phase HPLC on a phenyl column, and using single wavelength detection at 228 nm, yielded values in the range of 0.04% to 0.05% of the dry biomass for the taxol content. Portions of these extracts were then submitted to the National Cancer Institute at Frederick, Md. for confirmatory analysis. Their analysis, done with an HPLC equipped with a photo-diode array detector, indicated the presence of a substance with a large absorbance at 280 nm for the needle samples. The bark samples, all of the compounds in the taxol reference mixture, and pure taxol did not show this coeluting compound. The discovery of this impurity prompted us to attempt its isolation so that its presence within the taxol peak could be compensated for based on its spectral characteristics.

Since the interfering compound coeluted with taxol in the reversed phase system, we used a normal phase system to make the separation. A 27 g sample of *Taxus media* "Hicksii" needles was extracted with methanol-toluene and chromatographed on a 22 mm×250 mm column of silica gel. A rapid separation was made and 50% acetone in methylene chloride was used to strip the taxol fraction from the column. This extract was evaporated to dryness, redissolved in 9% acetone in methylene chloride, and placed on a second 22 mm×250 mm column of silica gel which had been equilibrated with 9% acetone in methylene chloride. A slow acetone gradient was begun and the acetone concentration was monitored spectrophotometrically at 270 nm.

Figure 3:
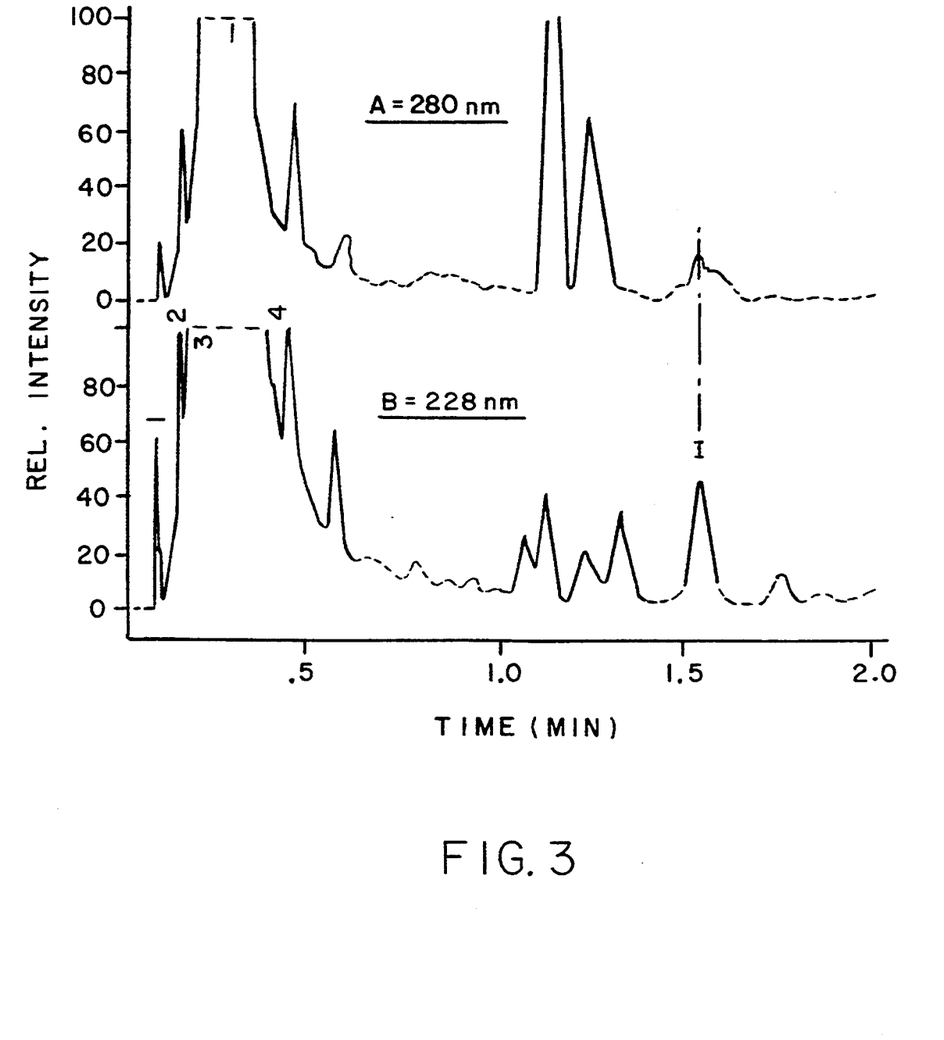
FIG. 3 depicts chromatograms of extractions from needle samples at 228 and 280 nm.

Thirteen 200 mL fractions were taken as the acetone concentration was gradually increased from 9% to 15%. Fraction #4 contained a pattern of peaks in the taxol retention time region that exactly matched the pattern of peaks seen at 280 nm in the chromatographic scan of needle samples (FIG. 3a and 3b). Spectral scans of these interfering peaks showed several common features. The interferences had absorption maxima very close to 280 nm, absorption minima close to 235 nm, and a response ratio of approximately 3.5 for A(280)/A(228).

Fraction #5 showed an absorption pattern similar to fraction #4; however, the quantity of material in this fraction was 38% that of fraction #4. Fractions #6, #7, and #8 showed decreasing mass with the same chromatographic pattern. Fraction #8 has essentially no mass. Taxol first appeared in fraction #9 as a large peak with only a small quantity of cephalomannine. Fraction #10 contained large peaks of both taxol and cephalomannine. These taxol fractions showed spectral scans identical to that of pure taxol and yielded a value of approximately 0.05 for A(280)/A(228).

Simultaneous equations were set up to calculate the PF (Purity Factor) of the taxol peak:

where $A(280) = AT(280) + AU(280)$
  $A(228) = AT(228) + AU(228)$
and $A(280)$ = Total absorbance at 280 nm
  $AT(280)$ = Absorbance due to Taxol at 280 nm
  $AU(280)$ = Absorbance due to the Unknown at 280 nm
where $K1 = AU(280)/AU(228) = $ ca 3.50
  $K2 = AT(280)/AT(228) = $ ca 0.05
and $K3 = A(280)/A(228)$ Then $PF = \dfrac{AT(228)}{A(228)} = \dfrac{K1 - K3}{K1 - K2}$ Substituting in our measured values for K2 and K1, the following was obtained:

$$PF = 1.0145 - 0.29 \times A(280)/A(228) \quad (2)$$

The above formula was used to correct experimental results. Most of the samples gave an absorbance ratio of approximately 0.35 which yielded 0.91 as the purity factor. Thus, values of the taxol content of the needles of the ornamental yew, *Taxus media* "Hicksii," measured to be 0.050% by reversed-phase HPLC on a phenyl column with absorbance at 228 nm were corrected to 0.046% on a dry biomass weight basis. Other workers who analyze for taxol using a phenyl bonded column should be aware of the possibility that their taxol peaks may contain underlying interferences and test for these interferences by running a spectral scan of the taxol peak and/or monitoring at 280 nm in addition to monitoring at 228 nm.

EXAMPLES

Example 1

Organic Phase Extractions

Several organic phase extraction techniques were employed for comparative purposes, in parallel with the critical fluid extraction and purification experiments. These techniques generically consisted of hexane washing, methanol (M)/methylene chloride (MC) extraction, three to four stages of methylene chloride-aqueous phase partitioning followed by evaporation to dryness and re-dissolution into methanol. A silica mini-column (1 cm long) was used to clean up very impure fractions prior to HPLC analysis.

First, the dry ground powder was washed with hexane to remove nonpolar waxes. Two procedures were utilized: Soxhlet extraction and mixing with a stir bar in an excess of hexane (10 ml/g) at room temperature the latter technique is referred to as the Snader technique. The elapsed time for this procedure was between 8 to 24 hours.

The hexane extract was taken to dryness, redissolved into hexane, filtered, and cleaned up on a silica mini-column using a hexane:acetone elutant. The hexane washed needles were dried and then extracted with a 50/50 mix of M/MC. This extraction by the Soxhlet technique was conducted for 3 hours and allowed to stand for another 12 to 15 hours; in the Snader technique, the sample was allowed to spin overnight. The crude M/MC extracts were evaporated to dryness and redissolved into MC. Equal aliquots of this fraction and distilled water were mixed and then allowed to partition in a separatory funnel.

The MC phase was drained into a rotary evaporator, and the aqueous phase re-extracted with MC (up to three more times). A small amount of methanol was used to break the water/MC emulsion formed with the Snader extract. The MC partitions were dried by rotary evaporation and tared. The dried MC extract was redissolved into methanol for HPLC analysis. The results of these experiments, as a percent of initial dry biomass weight for taxol and of dry extract weight for purity, are listed in Table 1.

posed surface area. The second sequence of experiments indicated that, as suspected, critical fluid extraction was controlled by solvent polarity. In this sequence, a sample was sequentially extracted with increasingly polar critical fluid solvents. The results of these experiments, all conducted at 3,000 psi and 60° C., are listed in Table 2.

TABLE 2

CRITICAL FLUID EXTRACTION AS A FUNCTION OF POLARITY

| EXP # | CRITICAL FLUID | POLARITY (debyes) | DENSITY (g/ml) | TAXOL (%) | PURITY (%) |
|---|---|---|---|---|---|
| TAXC-4 | $CO_2$ | 0.000 | 0.738 | 0.002 | 0.013 |
| TAXC-5 | $C_3H_8$ | 0.084 | 0.495 | 0.003 | 0.029 |
| TAXC-6 | $N_2O$ | 0.200 | 0.739 | 0.003 | 0.077 |
| TAXC-7 | Freon-22 | 1.400 | 1.145 | 0.016 | 0.416 |

In Table 2 above, percent taxol is based on the original dry sample mass and percent purity is based on extracted mass.

Example 3

Several experiments were conducted to confirm and improve the Freon-22, chlorodifluoromethane ($CHClF_2$), result. For example, TAXC-7 was conducted with 10 sample volumes of Freon-22 in only 20 minutes. Several experiments were conducted to evaluate the impact of volumetric throughput and residence time on extraction efficiency. Experiments were also conducted to determine if the very nonpolar waxes inhibited the mass transfer of taxol into the critical fluid phase. These experiments suggest that 100 sample volumes of critical fluid were more than sufficient to extract all the taxol from a sample, and that polar waxes did impede taxol mass transfer. Consequently, subsequent experiments were conducted with a minimum of 100 sample volumes of critical fluid solvent on either hexane-washed or supercritical fluid carbon dioxide (SCF $CO_2$) extracted needles. SCF $CO_2$, because of its nonpolarity and density at the conditions tested, behaves very much like hexane extracting about 7% of the polar waxes from the needles and no taxol.

TABLE 1

ORGANIC PHASE EXTRACTION OF TAXOL FROM NEEDLES

| | SOXHLET | | | SNADER | | |
|---|---|---|---|---|---|---|
| FRACTION | % EXT. | % TAXOL | % PURITY | % EXT. | % TAXOL | % PURITY |
| HEXANE | 7.3 | 0.003 | 0.056 | 6.3 | 0.002 | .044 |
| MC PART. | 6.5 | 0.048 | 0.735 | 7.6 | 0.049 | 0.695 |
| AQ PART. | 19.9 | 0.001 | 0.005 | 28.4 | 0.000 | 0.002 |
| TOTAL | 35.2 | 0.052 | — | 42.3 | 0.051 | — |

EXAMPLE 2

Critical Fluid Phase Extractions

Early experiments indicated that critical fluid extraction was impeded by the presence of water in the needles. Thus, all subsequent experiments were conducted on dry, milled needles of the ornamental yew in order to minimize mass transfer resistance and to maximize ex- In order to replace Freon-22 which is an ozone depleter, the polarity of SCF $CO_2$ was modified by the addition of methanol. Conditions of temperature, pressure and cosolvent were selected on the basis of a Hildebrand solubility parameter match to Freon-22 at 3,000 psig and 60C. The results of these experiments are listed in Table 3.

TABLE 3

EXTRACTION OF TAXOL BY SCF $CO_2$/21 MOL % METHANOL

| EXP # | PRESS. (psig) | TEMP. (C.) | TIME (min) | FLOWRATE (ml/min) | EXTRACT (%) | TAXOL (%) | PURITY (%) |
|---|---|---|---|---|---|---|---|
| TAXC-21 | 3,000 | 60 | 12.7 | 3.93 | 23.55 | 0.0491 | 0.209 |

TABLE 3-continued

| | EXTRACTION OF TAXOL BY SCF CO$_2$/21 MOL % METHANOL | | | | | | |
|---|---|---|---|---|---|---|---|
| EXP # | PRESS. (psig) | TEMP. (C.) | TIME (min) | FLOWRATE (ml/min) | EXTRACT (%) | TAXOL (%) | PURITY (%) |
| TAXC-22 | 1,259 | 40 | 40.7 | 1.28 | 21.29 | 0.0493 | 0.231 |

These experiments, based on an organic phase extraction/HPLC analysis of the residues, extracted about 99+% of the taxol available.

Example 4

Impact of Pressure and Temperature

The results of sensitivity experiments on pressure, temperature and methanol concentration are listed in Table 4.

TABLE 4

| | EXTRACTION OF TAXOL BY SCF CO$_2$/METHANOL | | | | | |
|---|---|---|---|---|---|---|
| EXP # | METHANOL (mol %) | PRESS. (psig) | TEMP. (C.) | TIME (min) | FLOWRATE (ml/min) | TAXOL (%) | PURITY (%) |
| TAXC-23 | 20.9 | 3,080 | 22 | 12.0 | 3.53 | 0.0359 | 0.270 |
| TAXC-24 | 20.9 | 3,080 | 41 | 17.1 | 2.93 | 0.0354 | 0.236 |
| TAXC-25 | 20.8 | 2,000 | 60 | 13.4 | 3.73 | 0.0480 | 0.278 |
| TAXC-26 | 20.8 | 3,000 | 60 | 18.6 | 2.69 | .0483 | 0.240 |
| TAXC-27 | 20.8 | 5,000 | 60 | 18.6 | 2.69 | 0.0389 | 0.165 |
| TAXC-28 | 0.0 | 1,259 | 41 | 20.8 | 2.46 | 0.0000 | 0.000 |
| TAXC-29 | 6.1 | 1,259 | 40 | 13.0 | 3.93 | 0.0256 | 0.463 |
| TAXC-30 | 11.1 | 1,259 | 40 | 14.0 | 3.64 | 0.0282 | 0.426 |

The average taxol content of the SCF extracts and the organic phase extracts of residues of the experiments listed in Table 4 was 0.0468±0.0022; no taxol was found in the residues of TAXC-25 and 26. TAXC-29 and TAXC-30 were the closest to the Freon result. (TAXC-7 in Table 2).

Example 5

Critical Fluid Extraction and Purification CXP

Freon-22, without the use of a polar modifier, was used to determine if a silica HPLC (Water's Microporasil) column could be used to selectively strip taxol out of the critical fluid phase. The results of these experiments are listed in Table 5.

TABLE 5

| | CRITICAL FLUID EXTRACTION AND PURIFICATION OF TAXOL AS A FUNCTION OF HPLC COLUMN BACK PRESSURE | | | | | | |
|---|---|---|---|---|---|---|---|
| EXP # | EXT. P (psig) | BACK P (psig) | T (C.) | t (min) | Q (ml/min) | EXTRACT (%) | TAXOL (%) | PURITY (%) |
| TAXC-32C | 3,000 | 1,960 | 60 | 52.8 | 4.75 | 0.99 | 0.0171 | 1.725 |
| TAXC-33C | 3,000 | 2,569 | 60 | 67.0 | 0.75 | 2.89 | 0.0176 | 0.607 |
| TAXC-34C | 3,000 | 1,500 | 60 | 6.0 | 8.33 | 2.34 | 0.0146 | 0.626 |

The foreruns of each of these experiments were collected in a 50:50 M:MC solvent trap. In each case, no taxol but a significant amount of mass was collected in the forerun. For example, 12.1% of the original dry sample mass was collected from the forerun of TAXC-34, which is designated as TAXC-34F. TAXC-34C in Table 5 refers to the material (2.3% of sample mass) which was selectively deposited onto the silica HPLC column. This mass, which was eluted from the column with methanol after the experiment was completed, was assayed by reversed-phase HPLC chromatography to contain 0.626% taxol. The residual concentration of taxol in the critical fluid treated sample, TAXC-34R, was determined to be 0.0324 % by organic phase extraction and reversed-phase HPLC analysis. The total taxol content of experiment TAXC-34 was thus 0.0470% of which 31.1% was recovered with a purification factor of 13 (0.626/0.047). The data listed in Table 5 suggests that the optimal results were obtained with a 2,000 psig back pressure in TAXC-32C which recovered 34.9% of the taxol with a purification factor of 35.

Example 6

CXP With Super Critical CO2/Polar Cosolvent

In order to replace Freon-22, several cosolvent systems with SCF CO$_2$ were evaluated. Methanol was no longer a cosolvent of choice because it would preferentially compete with taxol for adsorption sites on the silica column. This was confirmed in silica mini-column experiments and in a later experiment with the silica HPLC column. Cosolvents evaluated were methanol, methylene chloride, acetone, butanol and ethanol, each at 10 mole % in SCF CO$_2$ at 3,000 psig and 60° C.; all experiments were conducted with a back pressure of 2,000 psig. Taxol was found in significant quantities in the foreruns of experiments with methanol and ethanol as cosolvents; the results with butanol were ambiguous.

No taxol was found in the foreruns of experiments conducted with methylene chloride and acetone as cosolvents at 10 mole %. About half of the taxol (0.0242%) with a purification factor of 16 was recovered from the silica column in a methylene chloride cosolvent experiment (TAXC-36C). A SCF CO$_2$/acetone experiment (TAXC-37C) yielded less taxol (0.0147% with a purification factor of 15) from the silica column.

Example 7

CXP With Cradient Chromatography

The purification factor was further improved by chromatographically eluting out materials deposited on the head of the HPLC column. Because the history and retention behavior of the silica column was unknown, a gradient approach—proceeding from low polarity to moderate polarity was chosen. The results of these experiments are listed in Table 7.

cause SCF $CO_2$ with 18 mole % acetone was polar enough to spread taxol over the length of the column.

TABLE 7

CRITICAL FLUID EXTRACTION AND PURIFICATION OF TAXOL
AS A FUNCTION OF COSOLVENT CONCENTRATION AND PRESSURE

| EXP # | COSOLVENT | EXT. P (psig) | BACK P (psig) | TEMP (C.) | TIME (min) | Q (ml/min) | TAXOL (%) |
|---|---|---|---|---|---|---|---|
| TAXC-41C | 10% ACET | 3,000 | 2,000 | 60 | 5.8 | 4.75 | 0.0171 |
| TAXC-43C | 10% ACET | 2,000 | 1,650 | 41 | 25.0 | 2.00 | 0.0200 |
| TAXC-45C | 18% ACET | 2,000 | 1,585 | 41 | 40.8 | 1.23 | 0.0200 |
| TAXC-47C | 21% MC | 2,000 | 1,650 | 40 | 25.0 | 2.00 | 0.0200 |

The % taxol recovered from the silica column was determined by the difference between total taxol (an average of 0.047±0.0025% from seven experiments, TAXC-34 to 40) and taxol in the biomass residues; no taxol was seen in the foreruns. TAX-41C was chromatographically eluted with a hexane:methylene chloride:methanol gradient at a flowrate of 1.0 ml/min for 60 minutes. Twenty-five fractions were collected in tared vessels using absorbance at 228 nm as a guide; the collection vessel was changed at each valley in the chromatographic scan. The fractions were evaporated to dryness and weighed to determine extract weight. The fractions were then re-dissolved in a suitable quantity of methanol for conventional HPLC analysis on a reversed-phase phenyl column. A chromatogram of an assumed "taxol band" indicated that this fraction was made up primarily of taxol and cephalomannine. Analysis of adjacent bands indicate that about 95% of the taxol had eluted in the assumed "taxol band." The purity of taxol could not be ascertained because of the small amount of mass recovered; the purity was, however, estimated to be about 17% yielding a purification factor of approximately 360.

TAX-43C in Table 7 differs from TAX-41C by its critical fluid extraction, selective deposition and chromatographic elution conditions. For TAX-43C, a non-hexane washed sample was first extracted with 100 sample volumes of SCF $CO_2$ at 2,000 psig and 40C (TAXC-42) to remove waxes and other nonpolar constituents. The extract, which was 6.6% of the sample dry mass, contained no taxol. The residue from TAXC-42 was then extracted with SCF $CO_2$ containing 10 mole % acetone in TAXC-43. This extraction was conducted at 2,000 psig and 41C, conditions which would minimize capital and operating costs of a commercial unit. Additionally, the system was operated as close to isobaric as possible in order to minimize critical fluid recompression cost.

Figure 4A:
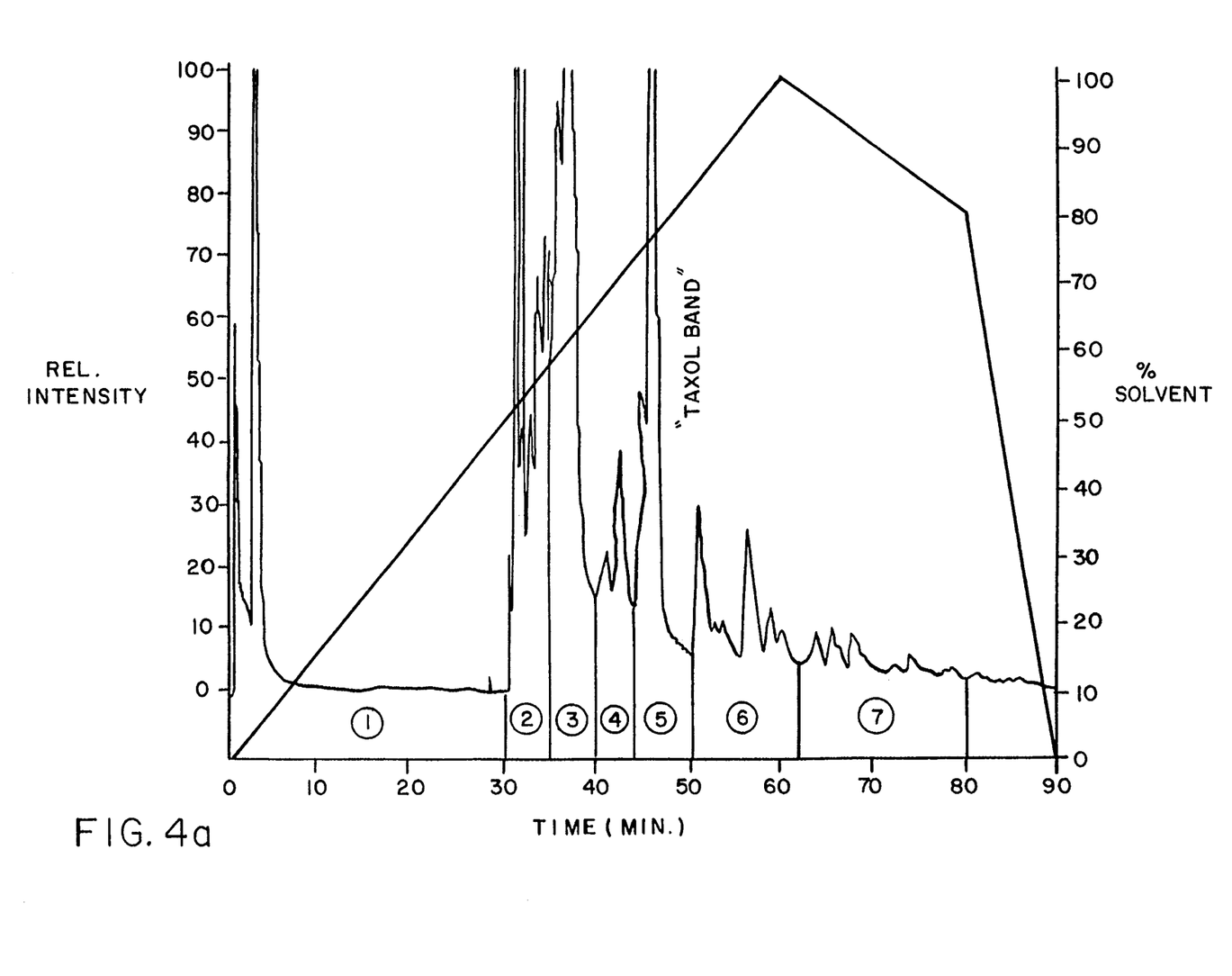
FIG. 4a and b depict chromatograms of fractions collected in accordance with a method of the present invention.
Figure 4B:
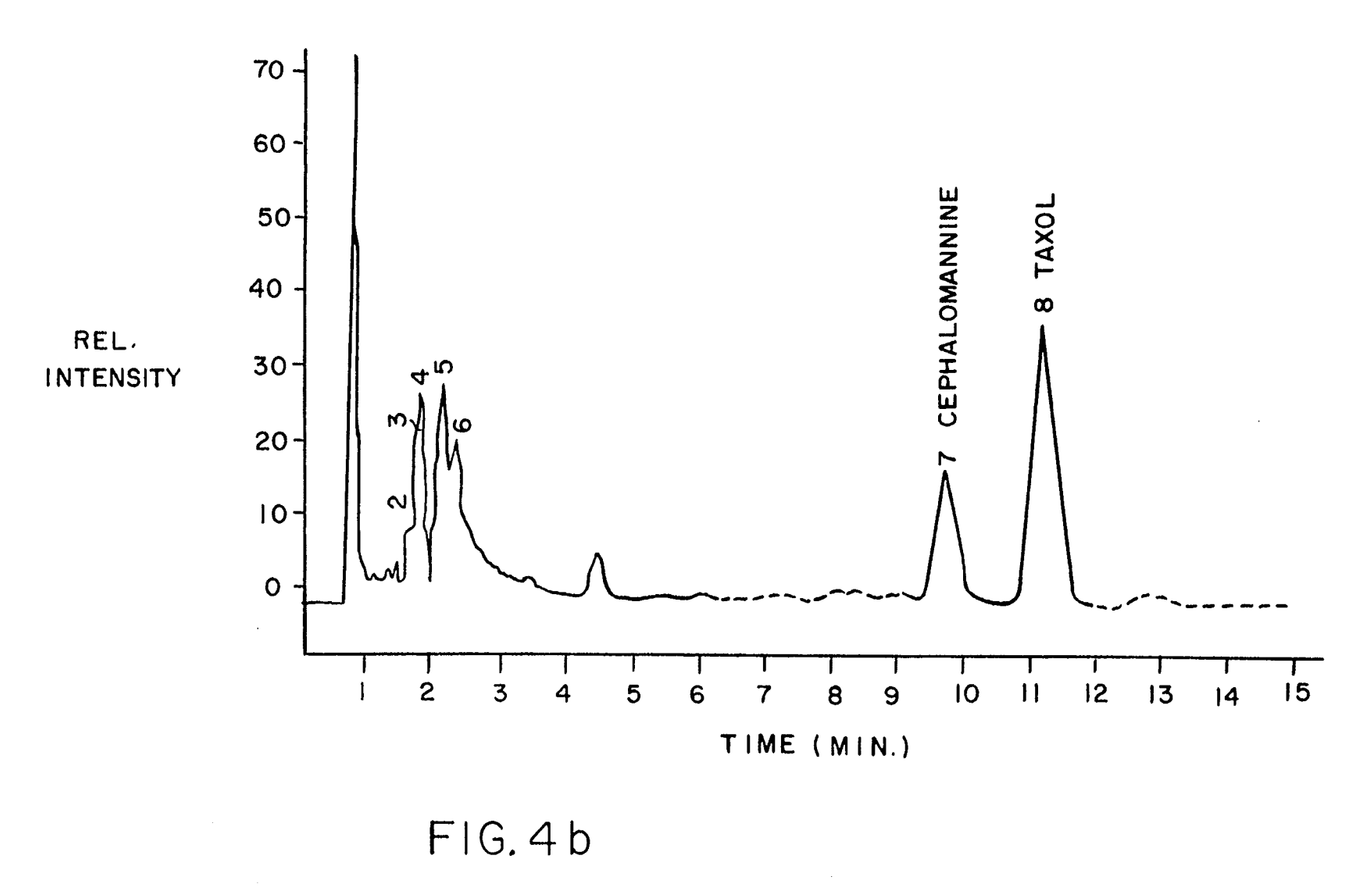

The deposited taxol and other impurities were chromatographically eluted from the silica column by a hexane:n-propanol:methanol ternary gradient which was extended to obtain increased resolution of fractions. In this run, only seven fractions were taken as shown in FIG. 4a. The fractions were collected in tared vessels, brought to dryness by rotary evaporation, re-dissolved in methanol and analyzed. An HPLC chromatogram of fraction #5, the assumed "taxol band," is shown in FIG. 4b. This scan indicates that the taxol band contained mainly taxol and cephalomannine. The purification factor was approximately 130 and the percent purity was 6.2% based on HPLC analysis and a weight of 4.0 milligrams for fraction #5.

TAXC-45C and TAXC-47C were conducted in the same manner as TAXC-43C; all three runs were preceded with an SCF $CO_2$ wash. In TAXC-45C, taxol did not chromatograph off the column in a sharp peak be- This was independently confirmed in experiments with a silica mini-column. In TAXC-47C, a high concentration of methylene chloride (21 mole %) in SCF $CO_2$ was effective in retaining taxol at the head of the HPLC column but was not as effective as a 21 mole % methanol cosolvent in extracting taxol from the raw biomass. The critical fluid extraction and chromatographic purification process described herein appears to be selective for taxol over cephalomannine. The concentration of taxol to cephalomannine in fraction #5 of TAXC-43C (see FIG. 4b) is 2.22 while the ratio in the needles was measured to be 1.08. Similar T/C ratios were obtained for TAXC-45C (2.04) and TAXC-47C (2.08).

Examination of the extract from SCF $CO_2$ washed samples and the foreruns of TAXC-43, 45 and 47 indicate that 10-deacetyl baccatin III and baccatin can be effectively separated from some of the polar solubles and taxol. We have discovered that these baccatins are very soluble in SCF $CO_2$ with a polar cosolvent at the conditions tested and can be selectively adsorbed onto a silica column at conditions of high polarity (greater than 20% acetone-conditions which favor its extraction and purification by critical fluids.

What is claimed is:

1. A method of extracting taxoids from taxoid containing source materials comprising the steps:
    a) dewaxing the source material by subjecting said source material to first fluid, which first fluid is comprised of a critical or near critical fluid, said waxes dissolving in the first fluid to form a wax laden extractant and a dewaxed source material;
    b) subjecting said dewaxed source material to a second fluid said second fluid comprising a critical or near critical fluid and a polar cosolvent, to form a taxoid extractant and waste material;
    c) separating taxoids from impurities in said taxoid extractant through chromatography means to produce a taxoid and an eluant.

2. The method of claim 1 wherein said chromatography means comprises at least one column.

3. The method of claim 2 wherein said chromatography means comprises a first column and a second column, said first column comprising a normal phase silica adsorption column for retaining taxoids and said second column comprising a reverse phase adsorption column for separating or purifying taxoids.

4. The method of claim 3 wherein said critical or near critical fluid and cosolvent are recycled until taxoids elute from said first column and thereafter directed to a second column, said taxoids being removed by said second column to produce a critical or near critical fluid/cosolvent mixture substantially free of taxoids.

5. The method of claim 4 wherein said taxoid free critical or near critical fluid/cosolvent mixture is depressurized allowing impurities to leave the solution to produce a critical or near critical fluid/cosolvent mixture substantially free of taxoids.

6. The method of claim 5 wherein said taxoids are eluted from said second column with a critical or near critical fluid and a polar cosolvent mixture to form a taxoid laden extractant, said taxoid laden extractant subjected to depressurization and heat to separate said taxoid from said eluant.

7. The method of claim 3 wherein said wax laden extractant is received by said first column, said first column retaining taxoids which elute in critical or near critical fluid/cosolvent mixtures.

8. The method of claim 7 wherein said taxoid extractant is received by said first column, said first column retaining taxoids and releasing said taxoids which elute in critical or near critical fluid cosolvent mixtures to form a first taxoid eluant, said first taxoid eluant depressurized to produce taxoids and a critical or near critical fluid/cosolvent mixture.

9. The method of claim 8 wherein said taxoids baccatin III and 10-deacetyl baccatin III are eluted from a first column.

10. The method of claim 8 wherein said purified taxoid produced upon depressurization is baccatin III and 10-deacetyl baccatin III.

11. The method of claim 8 wherein said taxoids retained in said first column are eluted from the column with a third fluid to form a second eluant, said third fluid comprising a mixture of a critical or near critical fluid and a polar cosolvent, said polar cosolvent present of greater polarity compared to said second fluid.

12. The method of claim 11 wherein said second eluant is directed to said second column, said second column retaining taxoids and releasing a mixture of a critical or near critical and cosolvent.

13. The method of claim 12 wherein said taxoids retained by said second column are eluted with a fourth fluid to form a taxoid eluant, said fourth fluid comprising a mixture of a critical or near critical fluid and a polar cosolvent, said cosolvent present in a concentration less than said second fluid.

14. The method of claim 13 wherein said taxoid eluant is depressurized to form taxoid and a mixture of a critical or near critical fluid and cosolvent mixture substantially free of taxoids.

15. The method of claim 14 wherein said taxoid produced upon depressurization is taxol and cephalomannine.

16. The method of claims 8, 12, or 14 wherein said mixture of critical fluid and cosolvent are recycled after taxoids are removed.

17. The method of claims 8, 12, or 14 wherein said critical or near critical fluid and cosolvent mixture is passed through an extractant cooler to form a purified critical or near near critical fluid and cosolvent which is recycled.

18. The method of claim 1 wherein said cosolvent is a polar solvent selected from the group of polar solvents consisting of methanol, ethanol, butanol, propanol methylene chloride and acetone.

19. The method of claim 1 wherein said supercritical fluid is comprised of one or more gases selected from the group consisting of carbon dioxide, fluoronated hydrocarbons and nitrous oxide.

20. The method of claim 1 wherein said taxoid is selected from one or more taxoids consisting of taxol, cephalomannine, baccatin III, 10-deacetyl baccatin III, deacetyltaxol, and deacetyl-7-epitaxol.

21. The method of claim 1 wherein said source material comprises needles.

* * * * *